(12) United States Patent
Decker et al.

(10) Patent No.: US 6,991,453 B2
(45) Date of Patent: Jan. 31, 2006

(54) OIL LAMP

(75) Inventors: DayNa Decker, Studio City, CA (US); Steven Dodson, Kneeland, CA (US)

(73) Assignee: Lumetique, Inc.

( * ) Notice: Subject to any disclaimer, the term of this patent is extended or adjusted under 35 U.S.C. 154(b) by 0 days.

(21) Appl. No.: 10/300,649

(22) Filed: Nov. 19, 2002

(65) Prior Publication Data

US 2004/0008509 A1 Jan. 15, 2004

Related U.S. Application Data

(60) Provisional application No. 60/331,904, filed on Nov. 19, 2001.

(51) Int. Cl.
*F23D 3/24* (2006.01)

(52) U.S. Cl. .................. 431/320; 431/298; 431/325; 126/45; 126/49

(58) Field of Classification Search ......... 431/320–325, 431/301, 313, 298, 302, 303, 291, 295, 322, 431/288, 305; 126/45, 49; 362/161, 159, 362/209
See application file for complete search history.

(56) References Cited

U.S. PATENT DOCUMENTS

| | | | |
|---|---|---|---|
| 214,085 A | 4/1879 | Beck | |
| 396,798 A | 1/1889 | Ambler | |
| 1,193,146 A | 8/1916 | Hoffman | |
| 1,579,949 A | 4/1926 | Peck | |
| 2,022,719 A | * 12/1935 | Irvine | 431/34 |
| 2,324,753 A | 7/1943 | Alexiade | |
| 3,162,030 A | * 12/1964 | Irving | 431/316 |
| 3,995,397 A | * 12/1976 | Despard, III | 47/81 |
| 4,557,687 A | * 12/1985 | Schirneker | 431/291 |
| 4,569,656 A | 2/1986 | Shimizu et al. | 431/325 |
| 4,805,076 A | 2/1989 | Menter | |
| 5,211,553 A | * 5/1993 | Menter | 431/320 |
| 5,307,799 A | 5/1994 | Scarnato et al. | 126/45 |
| 5,529,485 A | 6/1996 | D'Ambro et al. | 431/321 |
| 5,840,246 A | 11/1998 | Hammons et al. | 422/4 |
| 5,967,769 A | 10/1999 | Thompson | 431/288 |
| 6,068,472 A | 5/2000 | Freeman et al. | 431/291 |
| 6,086,644 A | 7/2000 | Nakatsu et al. | 44/275 |
| 6,099,877 A | 8/2000 | Schuppan | 426/104 |
| 6,159,002 A | 12/2000 | LeJeune | 431/324 |
| 6,562,294 B1 | 5/2003 | Smith | |
| 6,667,006 B2 | 12/2003 | Richards | |

* cited by examiner

*Primary Examiner*—S. Gravini
(74) *Attorney, Agent, or Firm*—Law Office of David Hong

(57) ABSTRACT

An oil lamp for providing a unique flame formation usable in a variety of decorative applications. The lamp includes a body that has an open upper end and that defines a chamber for carrying a combustible liquid. The lamp further includes a planar wick having a lower end located in the chamber of the body, for contacting the combustible liquid, and an upper end projecting upwardly from the open upper end. The wick may be positioned between first and second plates arranged in a spaced, confronting relationship to enhance capillary action or may be wrapped about a rigid plate. When lit, the lamp provides a unique flame formation. Optionally, the lamp may include scented oil and a conductive element to promote the release of fragrance upon heating, and the wick can be configured free of material having a high heat conductivity.

13 Claims, 9 Drawing Sheets

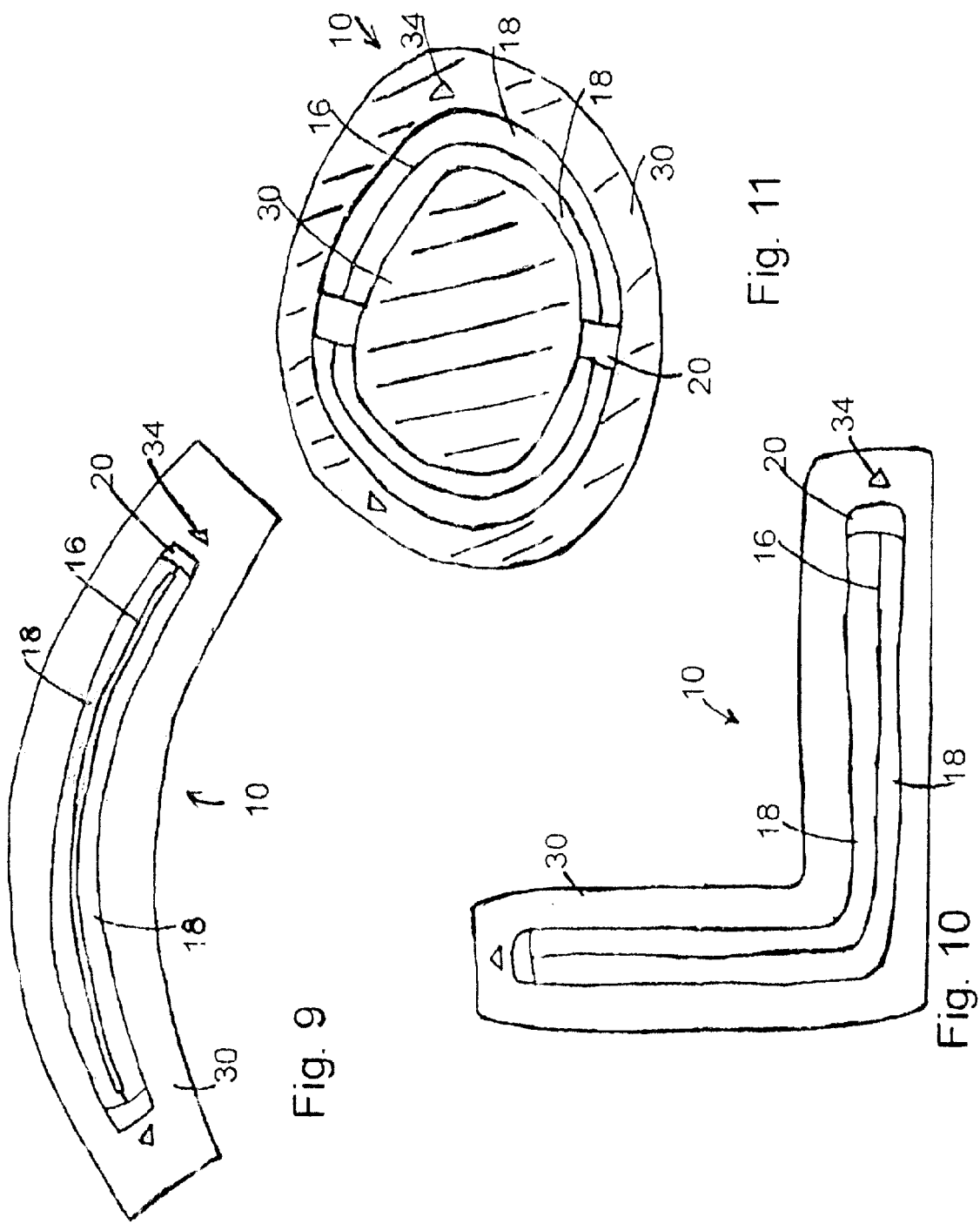

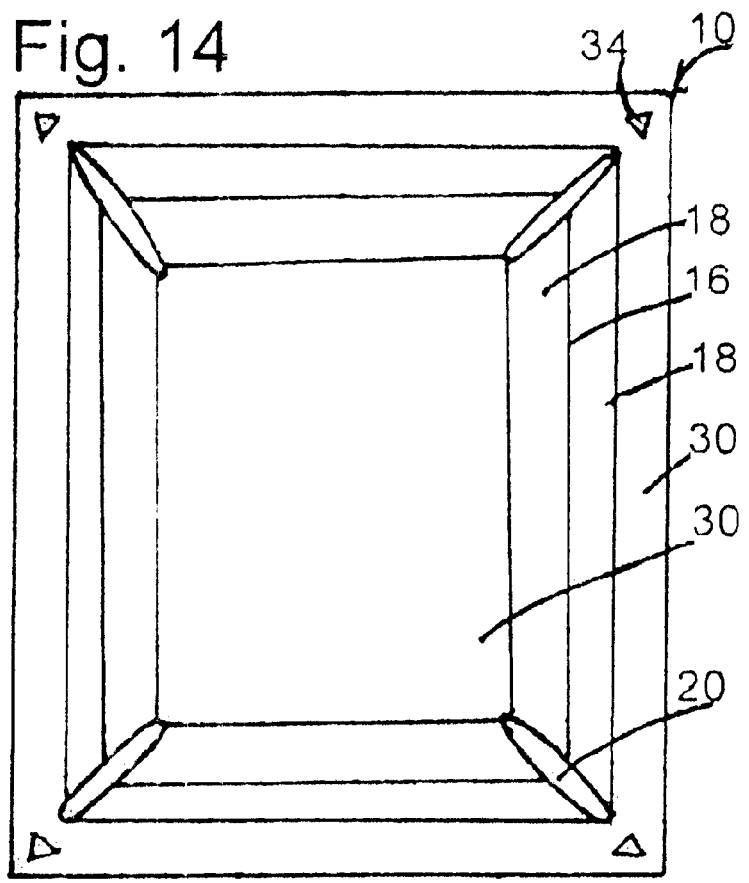

OIL LAMP

This application claims the benefit of U.S. Provisional Application No. 60/331,904, filed Nov. 19, 2001.

BACKGROUND OF THE INVENTION

The present invention relates generally to devices of illuminating and, more particularly, to oil lamps.

Oil lamps have long been used for decorative illumination and aromatic purposes. Such lamps typically include a body defining a chamber to hold a reservoir of combustible liquid and a wick to draw up the liquid through capillary action. The wick has an upper end extending out of an opening in the upper portion of the body and a lower end in contact with the reservoir of liquid. For effective capillary action, wicks typically are configured as a cord of fibers, such as cotton threads, braided in a rope-like configuration. When lit, the lamp forms a teardrop flame that is fed by the combustible liquid. Such lamps also may incorporate scented oil for aromatic purposes. Heat generated from the burning of the oil is conducted into the reservoir via the wick to promote the release of fragrance into the environment.

Although such lamps have been generally effective, current configurations are deficient in some respects. For example, the teardrop flame resulting from the wick's rope-like configuration can produce undesirable shadowing and otherwise limit decorative appeal. In addition, the release of fragrance in traditional lamps is tied to the wick's ability to conduct heat to the reservoir of scented oil; however, materials that promote capillary action, i.e., porous material, often are poor heat conductors. Thus, the release of fragrance is not optimal. To combat this, wicks often are provided with materials having a high heat conductivity, such as copper wiring, compromising capillary action.

It should, therefore, be appreciated there is a need for an oil lamp usable in a variety of decorative applications, providing a unique flame formation sustained by improved capillary action, and improved means for conducting heat into its scented oil reservoir for enhanced release of fragrance without the need of providing the wick with material having high heat conductivity. The present invention fulfills this need as well as others.

SUMMARY OF THE INVENTION

The present invention provides an oil lamp having a unique flame formation usable in a variety of decorative applications. The lamp includes a body that has an open upper end and that defines a chamber for carrying a combustible liquid. The lamp further includes a planar wick having a lower end located in the chamber of the body, for contacting the combustible liquid, and an upper end projecting upwardly from the open upper end. The wick may be positioned between first and second plates arranged in a spaced, confronting relationship to enhance capillary action and, when lit, the lamp provides a unique flame formation. Optionally, the lamp may include scented oil to promote the release of fragrance upon heating and the wick can be configured free of material having a high heat conductivity.

In a detailed aspect of a preferred embodiment of the invention, the lamp further includes a plurality of clips to clamp the plates and the wick together. At least one of the clips may include a top portion extending above and curved over the upper portion of the wick so that the wick's flame heats the clip and a bottom portion positioned to contact the reservoir of liquid, thereby conducting heat from the flame into the reservoir.

In another detailed aspect of a preferred embodiment of the invention, the plates are configured to hold wick such that the upper portion of the wick forms a selected decorative shape as viewed from above, e.g., arc, circle, square, triangle, heart or alpha-numeric shapes.

In another preferred embodiment, the wick is wrapped around a plate, e.g., aluminum, brass, glass, or steel.

Other features and advantages of the present invention should become apparent from the following description of the preferred embodiments, taken in conjunction with the accompanying drawings, which illustrate, by way of example, the principles of the present invention.

BRIEF DESCRIPTION OF THE DRAWINGS

Embodiments of the present invention will now be described, by way of example only, with reference to the following drawing figures:

FIG. 9–14 are top of various different shaped embodiments of the claimed invention.

DESCRIPTION OF THE PREFERRED EMBODIMENTS

Figure 1:
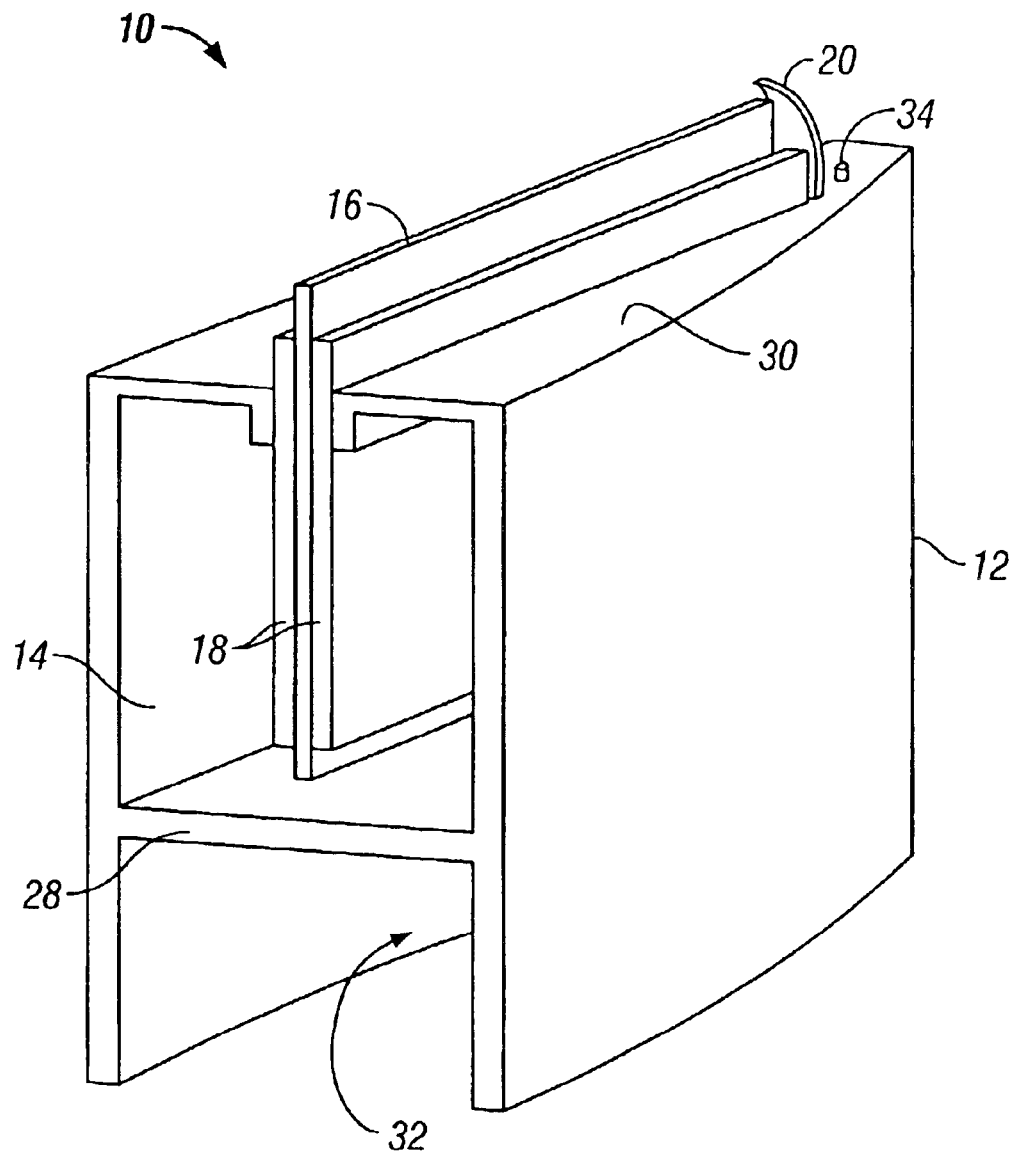
FIG. 1 is a cross-sectional perspective view of a preferred embodiment of an oil lamp in accordance with the present invention, the lamp having a body configured to hold an elongated wick.

With reference to the illustrative drawings, and particularly to FIG. 1, there is shown a lamp 10 having a body 12 that defines a chamber 14 to hold a combustible liquid and having a planar wick 16. For purposes of this disclosure, the term lamp refers to a device that is configured to illuminate. The lamp includes two plates 18 extending into the chamber and configured to secure and press the wick, to promote capillary action of the liquid up the wick. When lit, the lamp provides a unique flame formation usable in a variety of decorative applications. The body further includes conductive elements, clips 20 (only one of which is shown), configured to secure the plates and conduct heat from the flame into the reservoir of liquid that, when used with scented oil, promote the release of fragrance. Moreover, the present invention makes it unnecessary to configure the wick with enhanced heat conductivity.

Figure 2:
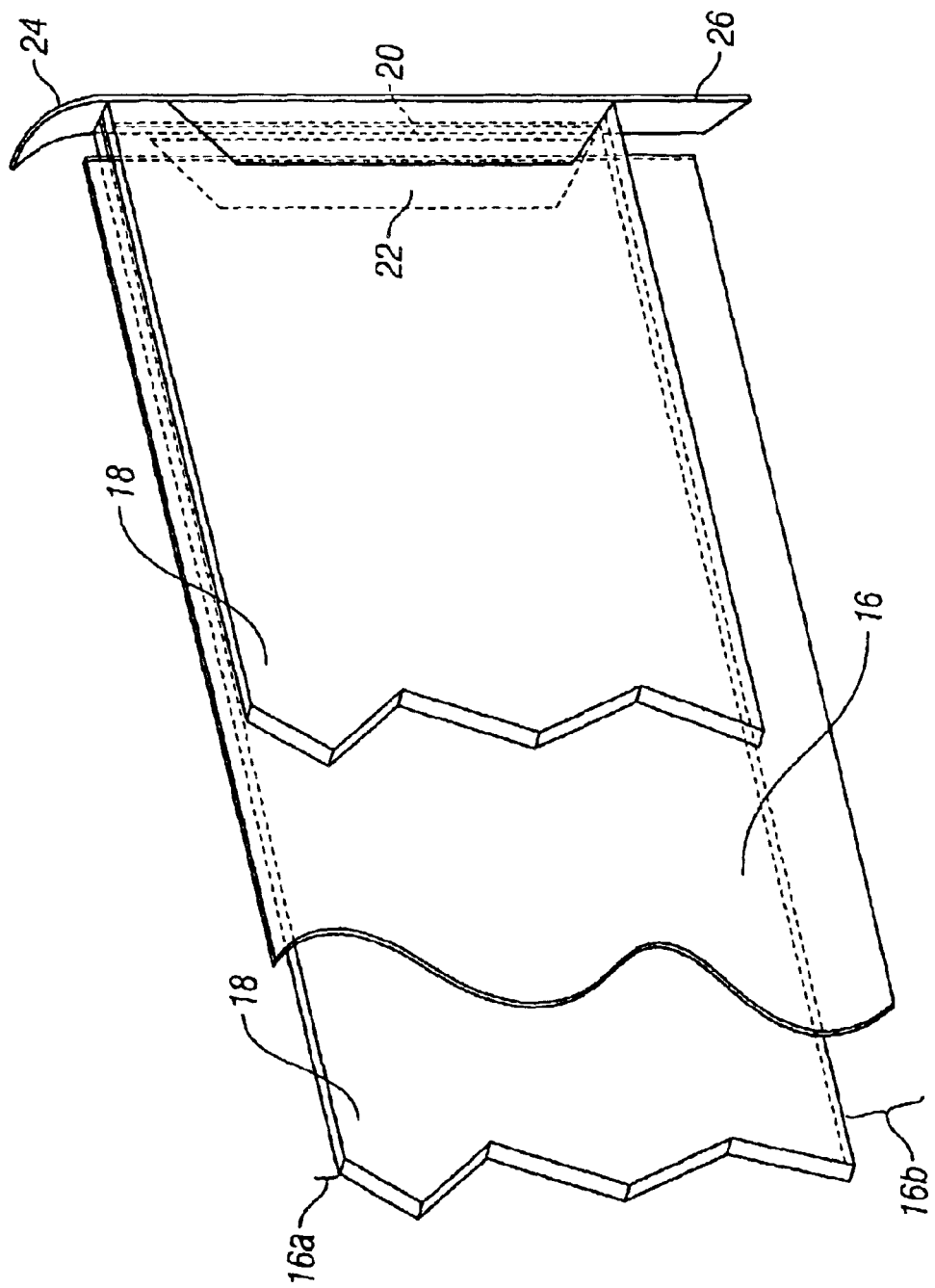
FIG. 2 is a partial perspective view of the wick, the plates, and the clips of the lamp depicted in FIG. 1.

With reference to FIG. 2, the clips 20 (only one of which is shown) are positioned on side edges of the plates. The clips include side flanges 22 that serve to press and support the wick between the plates, and by holding the wick in compression the clips enhance the capillary action of the liquid up the wick. The wick 16 is sized and positioned between the plates such that a top portion 16a extends out of the body of the lamp and a bottom portion 16b extends past the lower edge of the plates and contacts the liquid. In use, the top portion of the wick is lit so that a flame is present across the top portion of the wick conforming to the shape of the wick. In this embodiment, the wick is straight, but is should be appreciated that the wick and the plates may be configured in various shapes. For instance, the wick can be configured, when viewed from the top, in the shape of an arc, circle, square, triangle, heart, alphanumeric shapes, depending on the particular decorative use.

The material and thickness of the wick 16 are selected primarily to promote prolonged burning and capillary action with the liquid used. It is unnecessary to configure the wick with materials having high heat conductivity, e.g., stainless steel, aluminum, brass, bronze and the like. The wick can be a single sheet of fiberglass weighing approximately 8 ounces when the combustible liquid is a petroleum-based paraffin. In this embodiment, the wick is made of three sheets of fiberglass weighing approximately 24 ounces. The wick can also be made of cotton, carbon or any other material capable of prolonged burning and may be dyed into various colors to enhance aesthetic appeal. The top portion of the wick may be bound to avoid fringing of the burning end of the wick. In this embodiment, the top of the wick 16 extends approximately 1/16 inch to 1/4 inch above the plates and approximately 1/2 inch to 3/4 inch below the plates. The horizontal length of the wick is at least 1/4 inch narrower than the plates to ensure that the wick does not extend horizontally beyond the plates, which in turn avoids the spreading of flames to the top chamber 14 (FIG. 1). In this embodiment, the wick is preferably less than 3 inches high in the vertical direction to ensure upward travel of liquid to the top of the wick.

Figure 6:
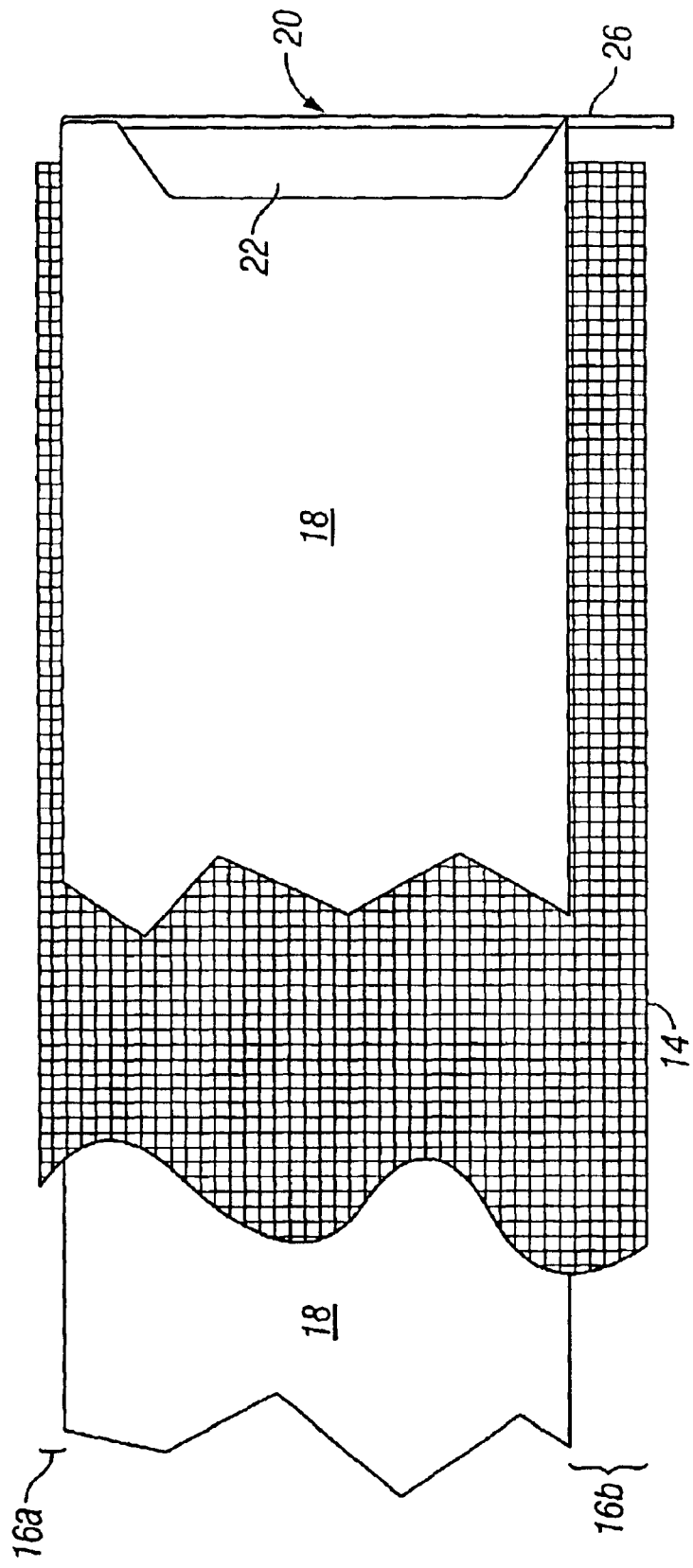
FIG. 6 is a cross-sectional perspective view of a wick, plate and alternate clip configuration for use with an oil lamp in accordance with the present invention.

With continued reference to FIG. 2, the clips 20 have a top portion 24 curved toward the wick 16 so that the flame from the wick heats the clip further includes a bottom portion 26 that extends into the reservoir of liquid. Each clip is made of a conductive material having a relatively high conductivity in comparison to the body 12 of the lamp 10. In this embodiment, each clip has a height of approximately 3.5 inches. The conducting element can be made of stainless steel, aluminum, brass, bronze or any other heat-conducting material. The bottom portion of the clip is positioned to contact the liquid and a shelf 28 (FIG. 1). In other embodiments the clips may not include a top portion (FIG. 6).

With reference to FIGS. 1 and 2, the plates 18 are suspended in the top chamber 14. In this embodiment, the plates 18 are at least 1/8 inch thick and made of glass or a similar material configured to withstand high temperatures without breaking, cracking or shattering. Each plate has a horizontal length of approximately 12.5 inches, a height of approximately 2 inches, and a thickness of approximately 1/8 inch. The plates extend at least 1/4 inch above a top surface 30 of the lamp 10 to reduce the conduction of heat to the body 12 of the lamp, and the plates do not contact the shelf 28 but rather are suspended at least 1/16 inch above the shelf using the clips. The top surface may have an indented portion (not shown) to hold scented oil. The plates are suspended above the shelf so that the wick can contact the liquid (not shown). In the alternative, the shelf incorporates a device (not shown) that supports the plates some distance above the surface of the shelf, thus requiring no top surface 30 from which to suspend the plates, which in turn may leave the top chamber 14 exposed. Optionally, the plate may be in contact with the shelf.

Figure 3:
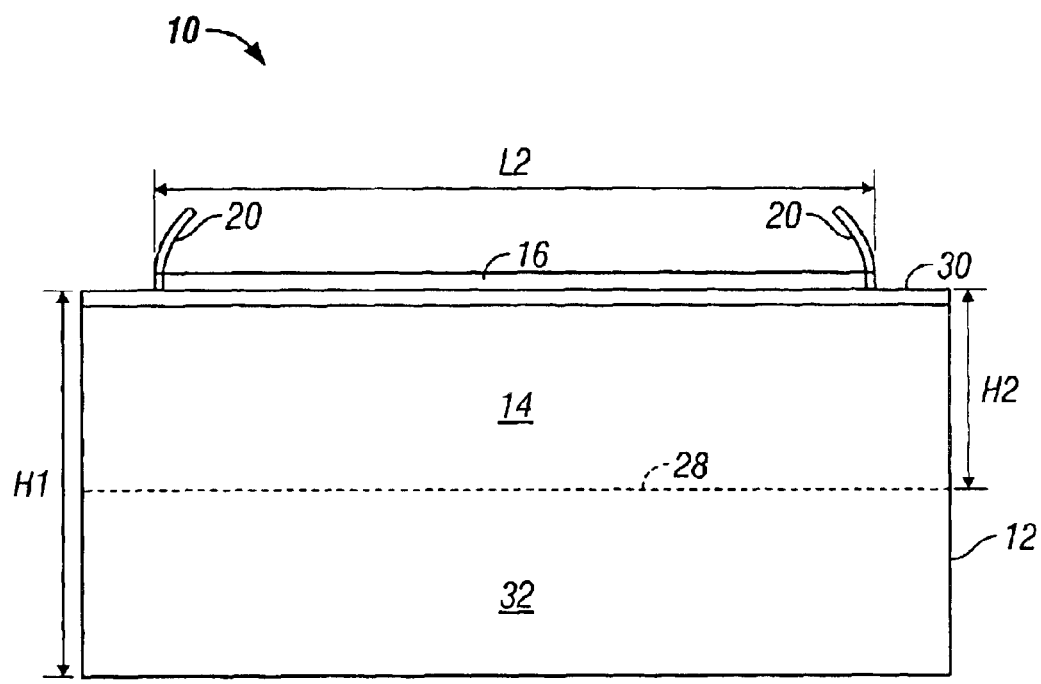
FIG. 3 is a side view of the lamp depicted in FIG. 1.
Figure 4:
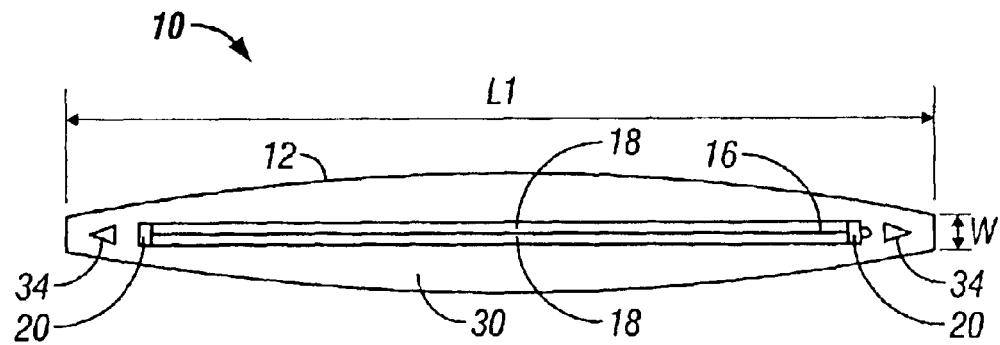
FIG. 4 is a top view of the lamp depicted in FIG. 1.

With reference FIGS. 1, 3 and 4, the body 12 of the lamp is eye shaped and has a height H1, here approximately 5.5 inches. However, it should be appreciated that the body of the lamp can be configured in any shape such as a circle, square, rectangle, polygon or curve. The body of the lamp is made from a material having a relatively low conductivity, which may be aluminum, steel, copper, brass, platinum, resin, or any other material. The external body of the lamp may be covered with an external veneer 13, which may include or resemble wood, leather, wax, porcelain, or a similar appearance with aesthetic appeal. The lamp has a length L1, here 15 inches, and a width W at each end, here 1 inch, but it should be appreciated that the lamp can come in a plurality of alternative sizes.

Figure 5:
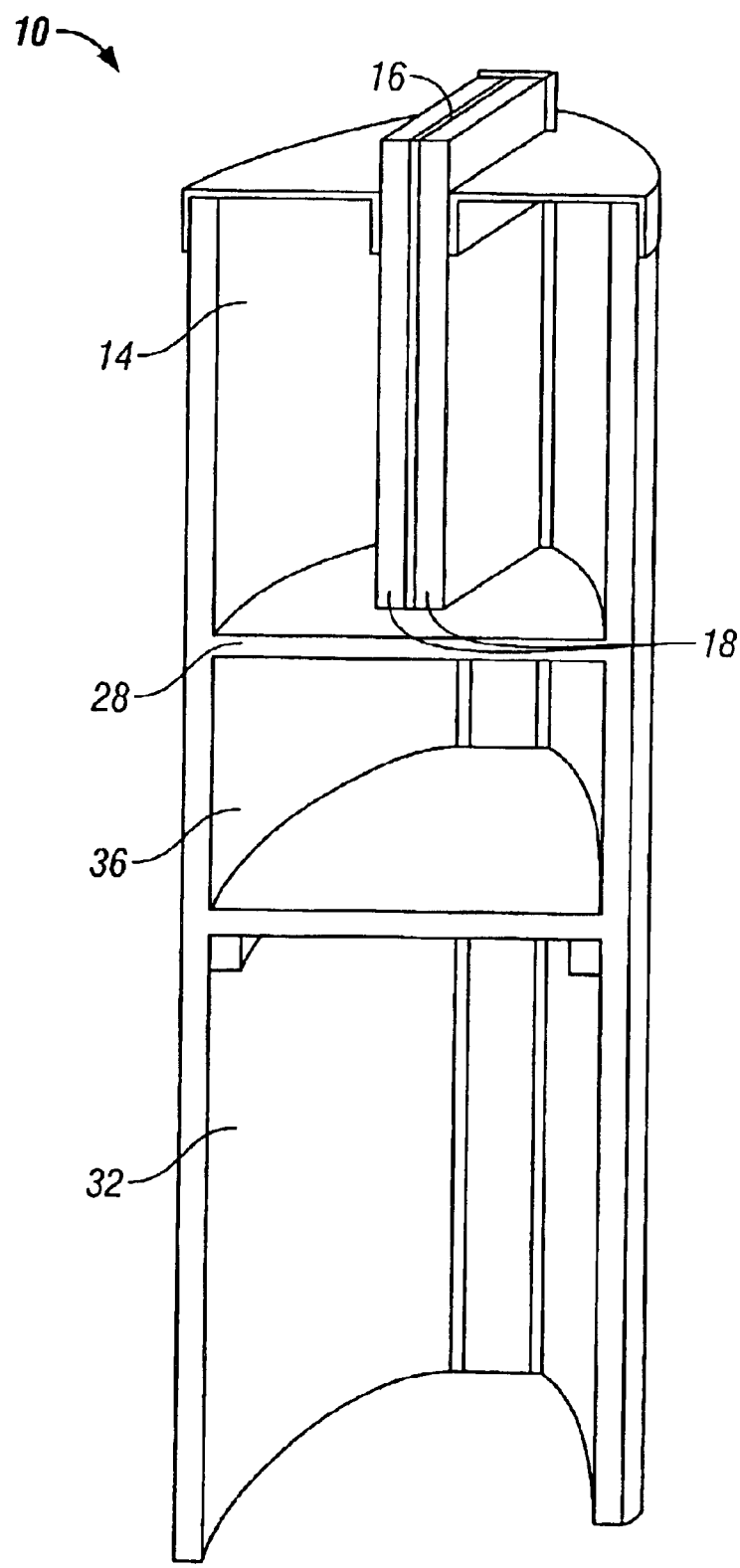
FIG. 5 is a cross-sectional perspective view of a second preferred embodiment lamp having three chambers in vertical alignment.

With continued reference to FIG. 1, the lamp has two chambers, the top chamber 14 and a bottom chamber 32 separated by the shelf 28. The top chamber 14, also referred to as an oil chamber, is configured to hold the liquid. In the preferred embodiment, the liquid is a vegetable based, non-toxic scented oil. Also, the liquid can be a petroleum-based paraffin or any other combustible fuel. The bottom chamber serves as an insulating chamber to reduce the rate at which the liquid loses heat through the shelf to the surface upon which the lamp rests and can be filled with a foam or other material to enhance the insulation. The lamp 10 further includes one or more holes 34 on the top surface 30 of the body 12 to allow for the filling and refilling of a liquid upon depletion. In the preferred embodiment, the holes are located at one or both ends of the horizontal alignment of the wick 16. The holes also promote the release of fragrance to the environment when the lamp contains a scented liquid. Chambers 14, 32 are in vertical alignment. Alternatively, the lamp can be configured to have only one chamber or to have a third chamber, a middle chamber 36 (FIG. 5).

Figure 7:
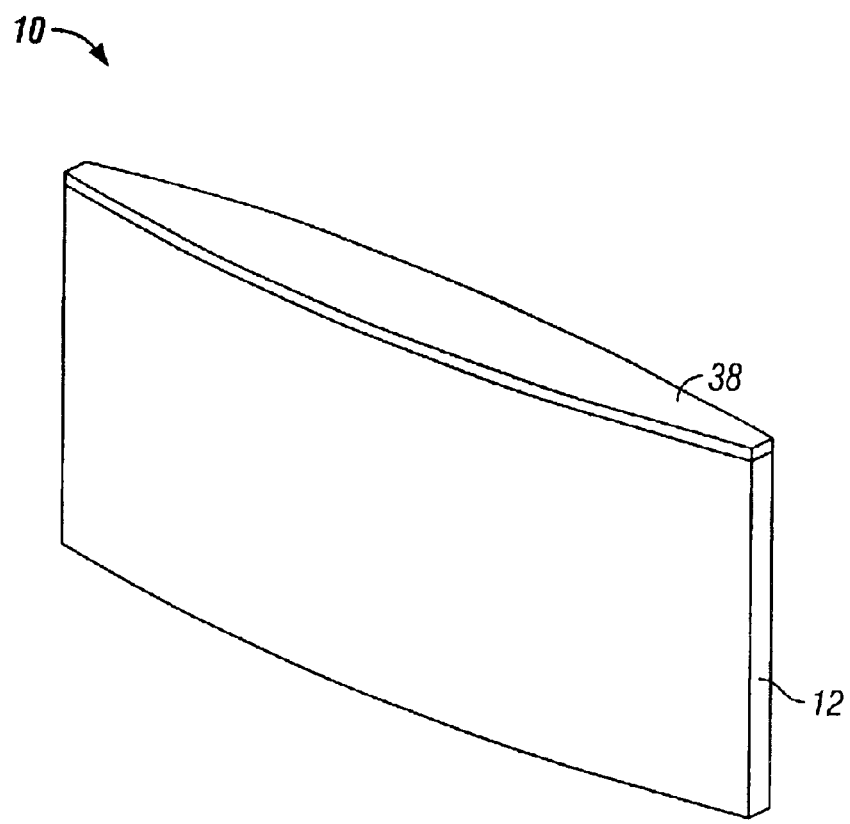
FIG. 7 is a perspective view of the lamp depicted in FIG. 1, incorporating an elongated lid.

With reference to FIG. 7, the lamp 10 is shown further including an elongated lid 38. The lid is configured to extinguish the wick by completely sealing off air to the flame and reservoir. To extinguish the wick, the user places the lid over the body 12. In one embodiment, the lid is configured to be secured to the body.

Figure 8:
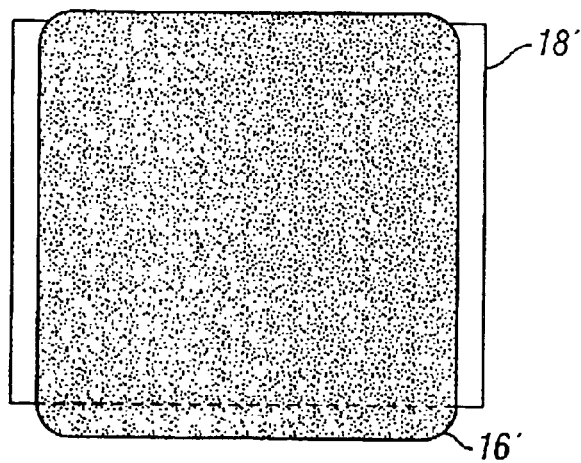
FIG. 8 is a perspective view of a second preferred embodiment of an oil lamp in accordance with the present invention, the lamp, with an elongated, planar wick folded about a metal plate.
Figure 13:
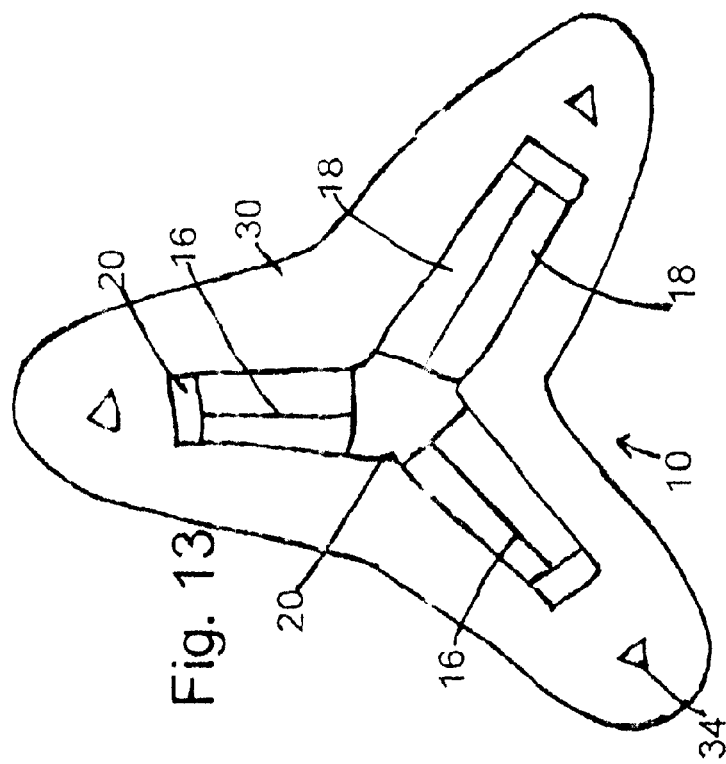
Figure 12:
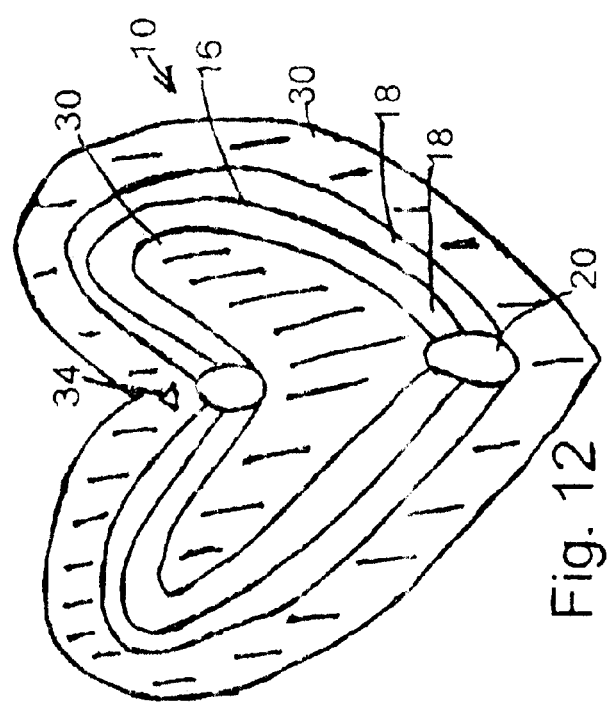

With now reference to FIG. 8, a planar wick 16' is configured as a sleeve about a rigid plate 18'. The plate is formed of aluminum and may be plated to enhance against erosion. The plate may also be formed of brass, steel, glass or other suitable materials. The wick is wrapped about the plate and stitched in place with a heat-resistant thread such as a fiberglass thread. Preferably, the wick is stretched taut about plate to further facilitate capillary action.

It should be appreciated from the foregoing description that the present invention provides an oil lamp usable in a variety of decorative applications that has a unique flame formation sustained by improved capillary action, and that has improved means for conducting heat into a scented oil reservoir for enhanced release of fragrance without the need of providing the wick with material having high heat conductivity.

The foregoing detailed description of the present invention is provided for the purposes of illustration and is not intended to be exhaustive or to limit the present invention to the precise embodiment disclosed. Accordingly, the scope of the present invention is defined by the following claims.

We claim:

1. An oil lamp comprising:
   a body defining a chamber for carrying a combustible liquid and having an open upper end; and
   a planar wick having a lower end located in the chamber of the body, for contacting the combustible liquid, and an upper end projecting upwardly from the open upper end, wherein the wick is free of material having a high heat conductivity;

first and second plates arranged in a spaced, confronting relationship with lower portions located within the chamber of the body and upper portions located adjacent to the open upper end; and at least one clip engaging peripheral edges of the first and second plates, wherein the planar wick is sandwiched between the first and second plates.

2. An oil lamp defined in claim 1, further comprising a conductive element having an upper portion extending above and curved over the upper portion of the wick and a bottom portion located in the chamber of the body.

3. An oil lamp defined in claim 1, wherein the wick is configured in a selected decorative shape as viewed from above.

4. An oil lamp comprising:

a body defining a chamber for carrying a combustible liquid and having an open upper end;

first and second plates arranged in a spaced, confronting relationship with lower portions located within the chamber of the body and upper portions located adjacent to the open upper end; and a planar wick sandwiched between the first and second plates and having a lower end located in the chamber of the body, for contacting the combustible liquid, and an upper end projecting upwardly from the upper portions of the first and second plates;

a plurality of clips positioned on side edges of the first and second plates to sandwich the planar wick between the plates; and at least one of the clips has a top portion extending above and curved over the upper portion of the wick, side flanges configured to hold the first and second plates and wick together, and a bottom portion located in the chamber of the body.

5. An oil lamp as defined in claim 4, wherein the plates are formed of glass and the wick is free of material having a high heat conductivity.

6. An oil lamp as defined in claim 4, wherein the first and second plates are configured to hold the wick such that the upper portion of the wick forms a selected decorative shape as viewed from above.

7. An oil lamp as defined in claim 6, wherein the selected decorative shape is selected from a group consisting of arc, circle, square, triangle, heart, and alpha-numeric shapes.

8. An oil lamp comprising:

a body defining a chamber for carrying a combustible liquid and having an open upper end;

first and second plates arranged in a spaced, parallel relationship with lower portions located within the chamber of the body and upper portions located adjacent to the open upper end;

a plurality of clips to clamp the first and second plates; and a planar wick sandwiched between the first and second plates and having a lower end located in the chamber of the body, for contacting the combustible liquid, and an upper end projecting upwardly from the upper portions of the first and second plates;

at least one of the clips has a top portion extending above and curved over the upper portion of the wick, side flanges configured to hold the first and second plates and wick together, and a bottom portion located in the chamber of the body.

9. An oil lamp as defined in claim 8, further comprising a lid configured to sit over the open upper end.

10. An oil lamp as defined in claim 8, wherein the plates are formed of glass and the wick is free of material having a high heat conductivity.

11. An oil lamp as defined in claim 8, wherein the first and second plates are configured to hold the wick such that the upper portion of the wick forms a selected decorative shape as viewed from above.

12. An oil lamp as defined in claim 11, wherein the selected decorative shape is selected from a group consisting of arc, circle, square, triangle, heart, and alpha-numeric shapes.

13. An oil lamp comprising:

a body defining a chamber for carrying a combustible liquid and having an open upper end; and a planar wick having a lower end located in the chamber of the body, for contacting the combustible liquid, and an upper end projecting upwardly from the open upper end, wherein the wick is free of material having a high heat conductivity;

first and second plates arranged in a spaced, confronting relationship with lower portions located within the chamber of the body and upper portions located adjacent to the open upper end; and the first and the second plates have substantially open and non-fused peripheral edges, wherein the planar wick is sandwiched between the first and second plates.

* * * * *